United States Patent
Penna (10) Patent No.: US 9,023,015 B2
(45) Date of Patent: May 5, 2015

(54) LAPAROSCOPIC INSTRUMENTS, ATTACHABLE END EFFECTORS AND METHODS RELATING TO SAME

(71) Applicant: Covidien LP, Mansfield, MA (US)

(72) Inventor: Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 14 days.

(21) Appl. No.: 13/756,777

(22) Filed: Feb. 1, 2013

(65) Prior Publication Data

US 2014/0221985 A1    Aug. 7, 2014

(51) Int. Cl.
*A61B 17/00* (2006.01)
*A61B 17/29* (2006.01)

(52) U.S. Cl.
CPC ........... *A61B 17/00234* (2013.01); *A61B 17/00* (2013.01); *A61B 17/29* (2013.01); *A61B 2017/00362* (2013.01); *A61B 2017/00477* (2013.01); *A61B 2017/2931* (2013.01); *A61B 2017/294* (2013.01); *A61B 2017/2946* (2013.01)

(58) Field of Classification Search
CPC ........ A61B 17/00; A61B 17/32; A61B 17/04; A61B 17/12; A61B 1/32
USPC ...................... 606/1, 169, 170, 205, 144, 174; 600/253, 235
See application file for complete search history.

(56) References Cited

U.S. PATENT DOCUMENTS

| | | | |
|---|---|---|---|
| 5,352,219 A * | 10/1994 | Reddy | 606/1 |
| 5,441,059 A | 8/1995 | Dannan | |
| 5,792,165 A * | 8/1998 | Klieman et al. | 606/170 |
| 5,817,119 A * | 10/1998 | Klieman et al. | 606/174 |
| 6,663,641 B1 * | 12/2003 | Kovac et al. | 606/144 |
| 6,673,092 B1 * | 1/2004 | Bacher | 606/205 |
| 7,666,181 B2 | 2/2010 | Abou El Kheir | |
| 7,691,126 B2 | 4/2010 | Bacher | |
| 7,901,398 B2 | 3/2011 | Stanczak et al. | |
| 8,021,358 B2 | 9/2011 | Doyle et al. | |
| 8,088,062 B2 | 1/2012 | Zwolinski | |
| 8,133,254 B2 | 3/2012 | Dumbauld et al. | |
| 8,162,973 B2 * | 4/2012 | Cunningham | 606/205 |
| 8,353,897 B2 | 1/2013 | Doyle et al. | |
| 2003/0060687 A1 * | 3/2003 | Kleeman et al. | 600/235 |

(Continued)

FOREIGN PATENT DOCUMENTS

| | | |
|---|---|---|
| EP | 1 400 211 | 3/2004 |
| WO | WO 98/01080 | 1/1998 |
| WO | WO 2008/005433 | 1/2008 |
| WO | WO 2012/112622 | 8/2012 |

OTHER PUBLICATIONS

European Search Report dated Apr. 29, 2014 in European Application No. 14 15 3551.

*Primary Examiner* — William Thomson
*Assistant Examiner* — Victor Shapiro (57) ABSTRACT

There is provided a method of attaching an end effector to a surgical instrument having a center rod with a distal tip. The method includes providing an end effector having a base and a coupler defining a pocket and movably mounted within the base. The end effector is moved over the center rod such that the distal tip of the center rod is seated within the pocket of the coupler. There is also disclosed an end effector including a base having a slot, a coupler movably mounted within the base and defining a pocket for receipt of a moving member of a surgical instrument and an operative member movably mounted on the base and connected to the coupler.

10 Claims, 10 Drawing Sheets

(56) References Cited

U.S. PATENT DOCUMENTS

| | | |
|---|---|---|
| 2005/0131396 A1 | 6/2005 | Stanczak et al. |
| 2008/0004656 A1* | 1/2008 | Livneh .......................... 606/205 |
| 2008/0287926 A1* | 11/2008 | Abou El Kheir ................. 606/1 |
| 2009/0209947 A1 | 8/2009 | Gordin et al. |
| 2012/0078290 A1 | 3/2012 | Nobis et al. |
| 2012/0078291 A1 | 3/2012 | Nobis et al. |
| 2012/0116433 A1* | 5/2012 | Houser et al. ................. 606/169 |
| 2012/0259325 A1 | 10/2012 | Houser et al. |

\* cited by examiner

LAPAROSCOPIC INSTRUMENTS, ATTACHABLE END EFFECTORS AND METHODS RELATING TO SAME

BACKGROUND

1. Technical Field

The present disclosure relates to a method of attaching end effectors to surgical instruments. More particularly, the present disclosure relates to surgical instruments and attachable end effectors and a method of remotely attaching end effectors to miniature laparoscopic surgical instruments within the body of a patient.

2. Background of Related Art

During various surgical procedures it is often necessary to assemble components of surgical instruments together within a body cavity of a patient or operative site. This may be necessary due to the construction of the surgical instrument itself or to minimize the size of incisions through a body wall of the patient. This is particularly true when the surgical instrument is relatively small and/or utilizes a relatively small size incision. It may additionally be done to exchange operative portions or end effectors of the surgical instrument within the body cavity during the operation without having to remove the entire instrument.

Current surgical instruments with exchangeable end effectors typically require multiple connection shafts to allow for attachment within the body cavity. The use of these multiple shafts may result in a relatively weak connection and can minimize the force available to be supplied to the end effector. Additionally, these multi-shaft connections require that the end effector be positioned substantially or directly in line with a shaft of the surgical instrument to perform the connection. This is difficult to accomplish in small spaces and requires precise alignment of the components prior to attachment. Still further, some sort of additional step is required to lock or secure the end effector to the shaft of the surgical instrument to complete the connection.

Therefore, there exists a need for a method of attaching an end effector remotely to a surgical instrument without the above complications. There also exists a need for an end effector which minimizes the number of connecting shafts to strengthen the connection. There further exists a need for an end effector which can initially accept the shaft of the surgical instrument at an angle rather than directly in line. There still further exists a need for an end effector which automatically locks itself to the shaft to complete the connection.

SUMMARY

There is disclosed a method of remotely attaching an end effector to a shaft of a surgical instrument. The method includes providing an end effector including a base having a first diameter, a coupler defining a pocket and movably mounted in the base and an operative member movably mounted on the base and connected to the coupler. A shaft of a surgical instrument is also provided and includes an elongate tubular member having a distal end of a second diameter and a center rod extending through the elongate tubular member. The center rod has a distal tip and a grove proximal to the distal tip.

To perform the disclosed method, the initially separated end effector is moved relative to the distal end of the elongate tubular member. The base of the end effector is approximated relative to the shaft such that the distal tip of the center rod passes into the base. The end effector is then manipulated relative to the shaft to seat the distal tip of the center rod within the pocket defined by the coupler.

The method further comprising the steps of forming a first incision in the body of a patient and inserting the shaft into the body of a patient through the first incision. A second incision is formed and the end effector is inserted into the body of the patient through the second incision.

In the disclosed method, the end effector is inserted through the second incision by holding the end effector within jaws of a grasping instrument and inserting the jaws of the grasping instrument and end effector through the second incision. The end effector is then moved relative to the shaft such that the end effector is oriented at a substantially right angle to the shaft. The base is approximated relative to the shaft by passing the distal tip of the center rod through a first slot in a first side of the base. The base is further approximated relative to the shaft by passing the distal tip of the center rod through a second slot in a second side of the base.

The end effector is manipulated relative to the shaft by moving the end effector through the right angle such that a longitudinal axis of the end effector is substantially parallel to a longitudinal axis of the shaft. The method further includes a step of positioning a distal end of the elongate member within a proximal opening of the base as the distal tip of the center rod is seated in the pocket of the coupler. The method still further includes the step of securing the distal tip of the center rod within the pocket of the coupler by biasing the center rod longitudinally relative to the coupler by a spring. In one embodiment of the disclosed method, the center rod is biased proximally relative to the coupler while in an alternative embodiment of the disclosed method the center rod is biased distally relative to the coupler.

There is also disclosed an end effector for remote attachment to a distal end of a surgical instrument. The end effector generally includes a base, at least one operative member movably mounted on the base and a coupler movably positioned within the base and connected to the at least one operative member. The base includes a first slot formed through a first side of the base and a second slot formed through a second side of the base. The base further includes a proximal opening for receipt of a distal end of an elongate tubular member associated with the surgical instrument.

The coupler includes a link connected to the at least one operative member, a distal portion and a collar proximal to the distal portion. The distal portion and the collar define the pocket therebetween. The distal member is a disk and the coupler includes a web portion connecting the disk to the collar. In a specific embodiment, the collar is C-shaped and defines a gap for passage of a center rod of the surgical instrument.

There is further disclosed a surgical instrument for remote assembly within the body of a patient. The surgical instrument generally includes a handle housing and an elongate tubular member extending distally from the handle housing. A center rod is movably mounted within the handle housing and elongated tubular member and has a distal tip and a groove proximal of the distal tip. The surgical instrument further includes an end effector having a base, an operative member movably attached to the base. The end effector also includes a coupler connected to the operative member and defining a pocket for receipt of the distal tip of the center rod. The pocked is defined between a distal disk of the base and a proximal C-shaped collar of the base.

DESCRIPTION OF THE DRAWINGS

An embodiment of the presently disclosed miniature laparoscopic surgical instrument and attachable end effector and method of attachment within the body of a patient are disclosed herein with reference to the drawings, wherein.

DETAILED DESCRIPTION OF EMBODIMENTS

An embodiment of the presently disclosed surgical instrument and remotely attachable end effector will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component farther away from the user.

Figure 1:
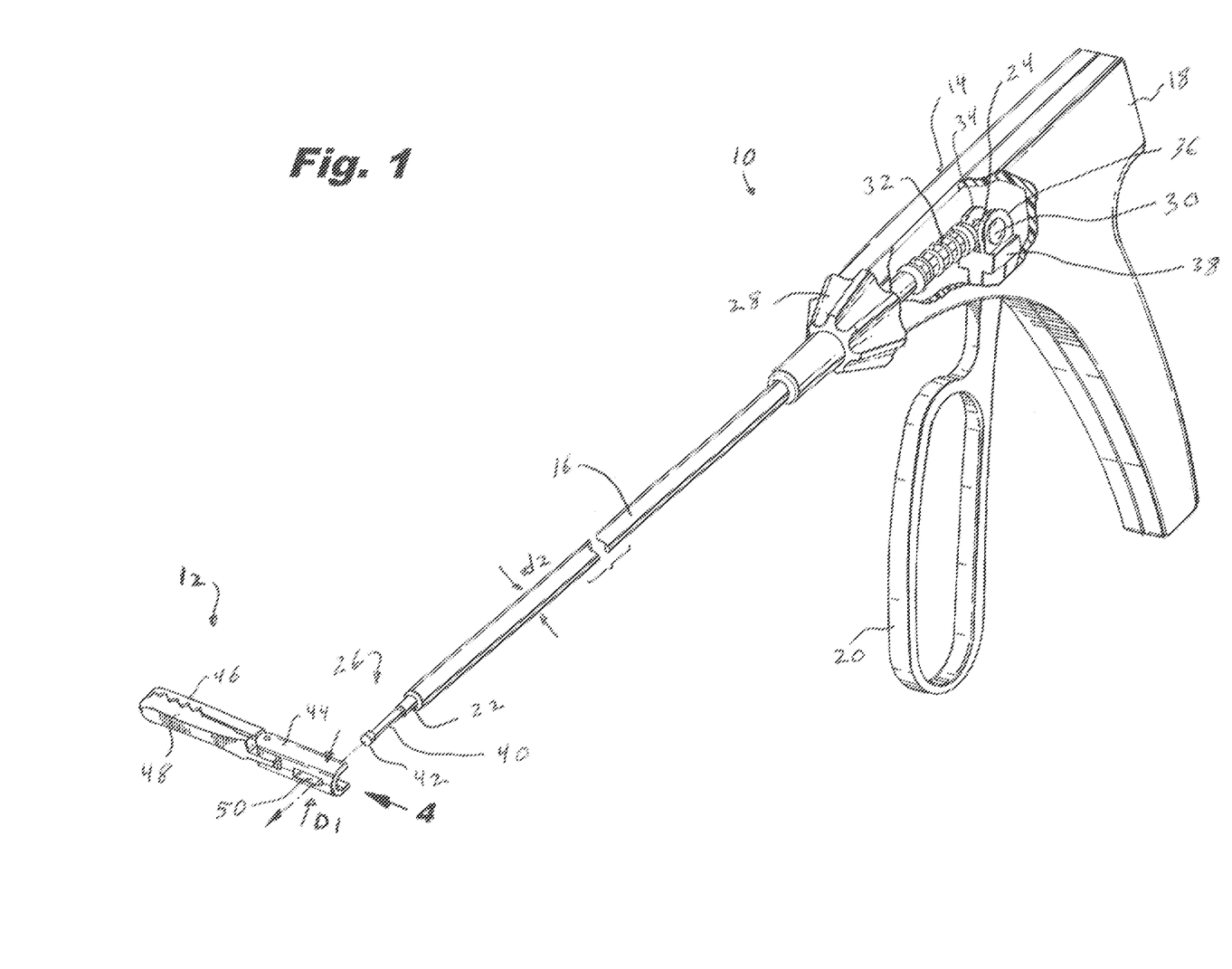
FIG. 1 is a perspective view in partial cross section of a laparoscopic surgical instrument and a remotely attachable end effector.

Referring to FIG. 1, there is disclosed a laparoscopic surgical instrument 10 and remotely attachable end effector 12. End effector 12 is provided to be remotely connected to surgical instrument 10 within the body of a patient in a "quick connect" fashion as described in more detail herein below. This permits multiple types of end effectors to be provided on surgical instrument 10 without removing surgical instrument 10 from within the body of the patient.

Surgical instrument 10 generally includes a handle assembly 14 and an elongate tubular member 16 extending distally from handle assembly 14. Handle assembly 14 includes a handle housing 18 and a trigger 20 pivotally mounted on handle housing 18. A center rod 22 is provided to connect to and operate end effector 12 and extends from within handle housing 18 through elongate tubular member 16. A proximal end 24 of center rod 22 is connected to trigger 20 while a distal end 26 of center rod 22 is attachable to end effector 12.

Handle assembly 14 additionally includes a rotation knob 28 to rotate elongate tubular member 16 and end effector 12 relative to handle housing 18. A pivot pin 30 secures proximal end 24 of center rod 22 to trigger 20 and a compression spring 32 is provided within handle housing 18 to bias center rod 22 proximally within handle housing 18. Specifically, pivot pin 30 extends through a pair of ears 34 and 36 on an upper end 38 of trigger 20 to secure proximal end 24 of center rod 22 to trigger 20. Movement of trigger 20 toward handle housing 18 drives center rod 22 distally within elongate tubular member 16, against the bias of compression spring 32, to actuate end effector 12.

End effector 12 generally includes a base 44 and first and second jaws 46 and 48, respectively, pivotally mounted on base 44. A slot 50 is formed through base 44 and is sized to accommodate distal end 26 of center rod 22 as described herein below. It should be noted that end effector 12, and in particular base 44, has a width or diameter D1 greater than a diameter d2 of elongate tubular member 16.

Figures 2, 3, 4:
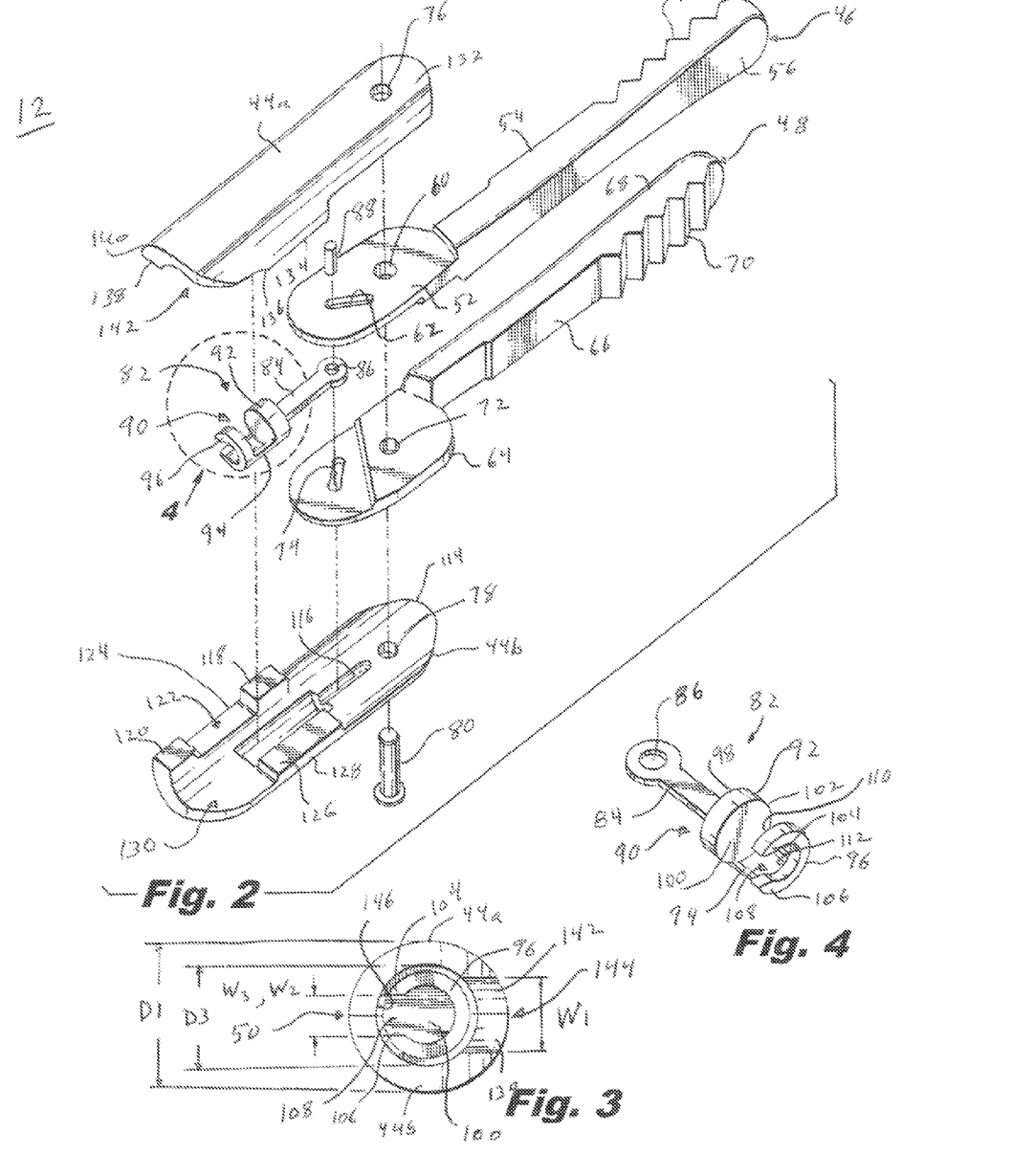
FIG. 2 is a perspective view, with parts separated, of the end effector incorporating a coupler for connection with the surgical instrument.
FIG. 3 is an end view of a coupler of the end effector.
FIG. 4 is a perspective view of the coupler.

Referring now to FIGS. 2-4, and initially with regard to FIG. 2, end effector 12 will now be described in detail. Base 44 is formed as complementary halves 44a and 44b. Complimentary halves 44a and 44b are attached in known fashion such as, for example, gluing, welding, etc. First jaw 46 includes a proximal portion 52, a center portion 54 and a distal portion 56. Distal portion 56 is provided with inwardly facing, tissue gripping teeth 58. Proximal portion 52 includes a pivot hole 60 about which first jaw 46 pivots relative to base 44 and a drive slot 62. Similarly, second jaw 48 includes a proximal portion 64, a center portion 66 and a distal portion 68 having inwardly facing, tissue gripping teeth 70. Proximal portion 64 also includes a pivot hole 72 and a drive slot 74. Base halves 44a and 44b have respective pivot holes 76 and 78. A pivot pin 80 extends through pivot hole 78 in base half 44b, pivot holes 72 and 60 of second and first jaws 48 and 46 and into pivot hole 76 in base half 44a. Pivot pin 80 forms a friction fit within pivot holes 76 and 78 in base halves 44a and 44b to further secure the base halves together, while allowing movement of the jaws.

In order to actuate first and second jaws 46 and 48, end effector 12 is provided with a connector or coupler 82 which is configured to receive distal end 26 of center rod 22 in quick connect fashion. Coupler 82 includes a distally extending arm or drive link 84 having a hole 86. A drive pin 88 is provided and extends through hole 86 in drive link 84 and rides within drive slots 62 and 74 in first and second jaws 46 and 48, respectively. Thus, movement of coupler 82 distally and proximally within base 44 cams first and second jaws 46 and 48 between closed and open positions. Coupler 82 additionally includes a proximal coupling portion 90 extending proximally from drive link 84. Coupling portion 90 is configured to receive distal end 26 of center rod 22.

Referring to FIGS. 2-4, coupling portion 90 of coupler 82 is formed as a semi-cylindrical member including a driving disk 92, a rigid intermediate, arcuate web 94 extending proximally from driving disk 92 and a semi-circular, C-shaped collar 96. Coupler 82 may be formed integrally by molding, milling, etc. or may be assembled from the various components.

Referring for the moment to FIG. 4, drive link 84 extends from a distal side 98 of driving disk 92 while a driven surface 100 is provided on a proximal side of driving disk 92. Collar 96 is C-shaped having ends 104 and 106 which define a gap 108 therebetween. Collar 96 includes a drawn surface 110 on a distal side 112. Driven and drawn surfaces 100 and 110 are engaged by distal tip 42 of center rod 22 (FIG. 1) to move coupler 82 within base 44.

With continued reference to FIG. 2, base half 44b has a distal end 114 through which pivot hole 78 is formed. A groove 116 is provided in base half 44b to allow for movement of drive pin 88. Base half 44b is provided with projections 118 and 120 defining a cut out 122 on a first side 124 of base half 44b. Cut out 122 forms half of slot 50 in base 44 described hereinabove. A single projection 126 extends from a second side 128 of base half 44b and, together with projection 120 defines a radial cutout 130 for receipt and passage of elongate tubular member 16 and center rod 22. Base half 44a is formed as a mirror image of base half 44b and includes a distal end 132. A projection 134 on a first side 136 and a projection 138 on a second side 140 define a matching radial cutout 142 similar to radial cutout 130 in base half 44b.

As best shown in FIG. 3, radial cutouts 130 and 142 of base halves 44a and 44b combine to form a gap or side entry opening 144 having a width W1 greater than and large enough to accommodate diameter d2 of elongate tubular member 16 (FIG. 1). Gap 108 defined between ends 104 and 106 of collar 96 has a width W2 which is greater than the diameter d3 of distal tip 42 of center rod 22 (FIG. 7) but is less than diameter d2 of elongate tubular member 16. In this embodiment, the width W3 of slot 50 in base 44 is equal to width W2 of gap 108 in collar 96. This allows distal tip 42 of center rod 22 to be inserted through coupler 82 and base 44 at a right angle to base 44. Additionally, radial cutouts 130 and 142 form a proximally facing opening 146 having a diameter D3 which is greater than diameter d2 of elongate tubular member 16 (see also, FIGS. 5-7).

Figures 5, 6, 7:
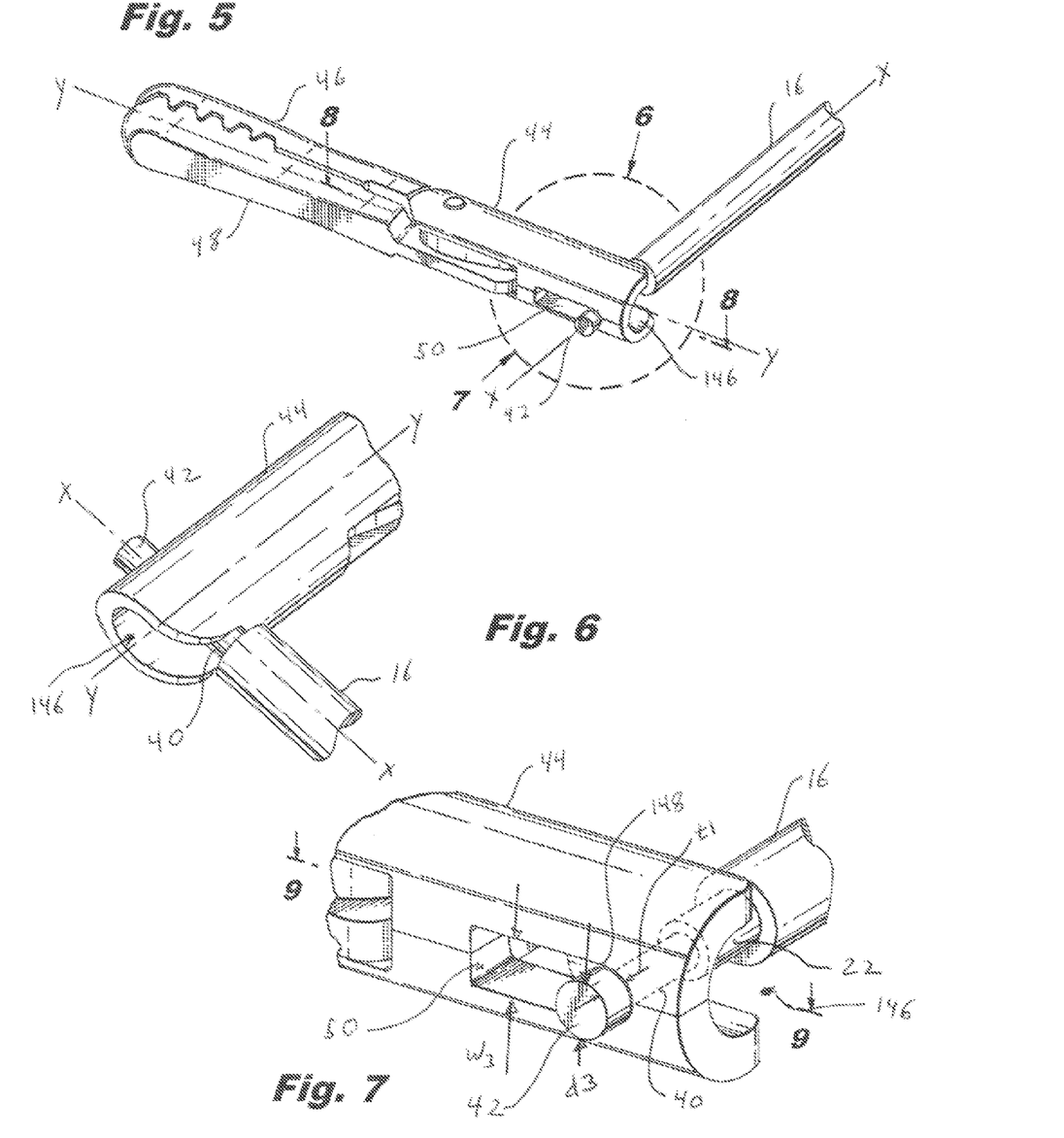
FIG. 5 is a perspective view of an inner shaft or center rod of the surgical instrument initially inserted into the end effector.
FIG. 6 is an enlarged area of detail view of FIG. 5.
FIG. 7 is an enlarged area of detail view of FIG. 5.

Referring now to FIGS. 1 and 5-13, and initially to FIGS. 5-9, the method of attachment of end effector 12 to elongate tubular member 16 and center rod 22 of surgical instrument 10 will now be described. Referring to FIG. 1, end effector 12 is positioned approximately at a right angle to elongate tubular member 16. End effector 12 is then moved toward distal end 26 of center rod 22, such that distal tip 42 of center rod 22 passes through slot 50 in base 44 of end effector 12 (FIGS. 5 and 6). Specifically, in this embodiment, end effector 12 is moved toward elongate tubular member 16 at a substantially right angle such that a longitudinal axis x-x of elongate tubular member 16 is perpendicular to a longitudinal axis y-y of base 44 of end effector 12.

Referring to FIG. 7, and as noted hereinabove, distal tip 42 of center rod 22 has a diameter d3 which is less than width W3 of slot 50. Distal tip 42 is positioned within a proximal end 148 of slot 50 and in a position to be rotated through slot 50. Distal tip 42 is formed as a cylindrical disk 150 having a thickness t1.

Figure 8:
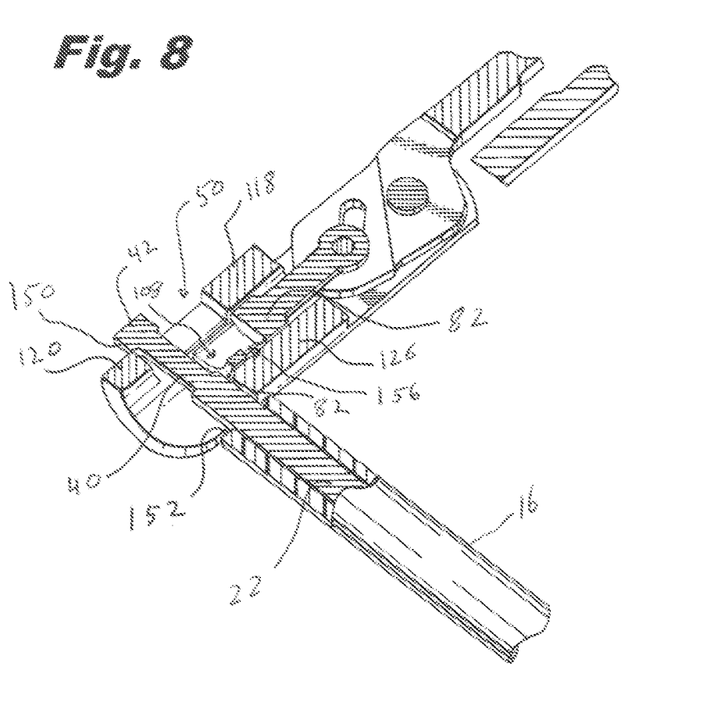
FIG. 8 is a perspective, cross-sectional view taken along line 8-8 of FIG. 5.
Figure 9:
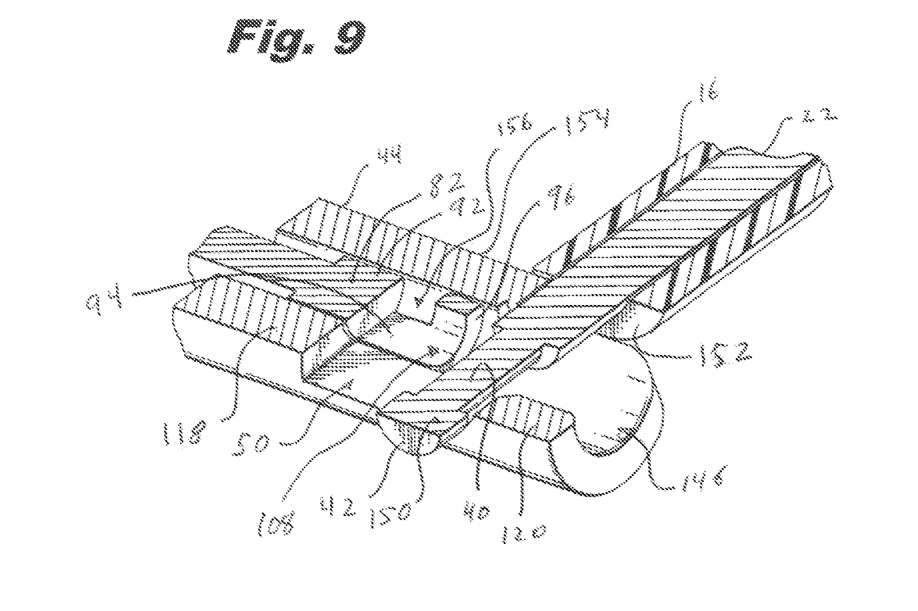
FIG. 9 is a perspective, cross-sectional view taken along line 9-9 of FIG. 7.

Referring now to FIGS. 8 and 9, in this initial position, an end face 152 of elongate tubular member 16 is adjacent to an outer surface 154 of base 44 of end effector 12. Disk 150 of center rod 22 is in a position to be rotated through slot 50 in base 44 and through gap 108 in collar 96 of coupler 82 until disk 150 seats into a pocket 156 formed between driving disk 92 and collar 96. Web 94 of coupler 82 prevents disk 150 from rotating out of coupler 82.

Figure 10:
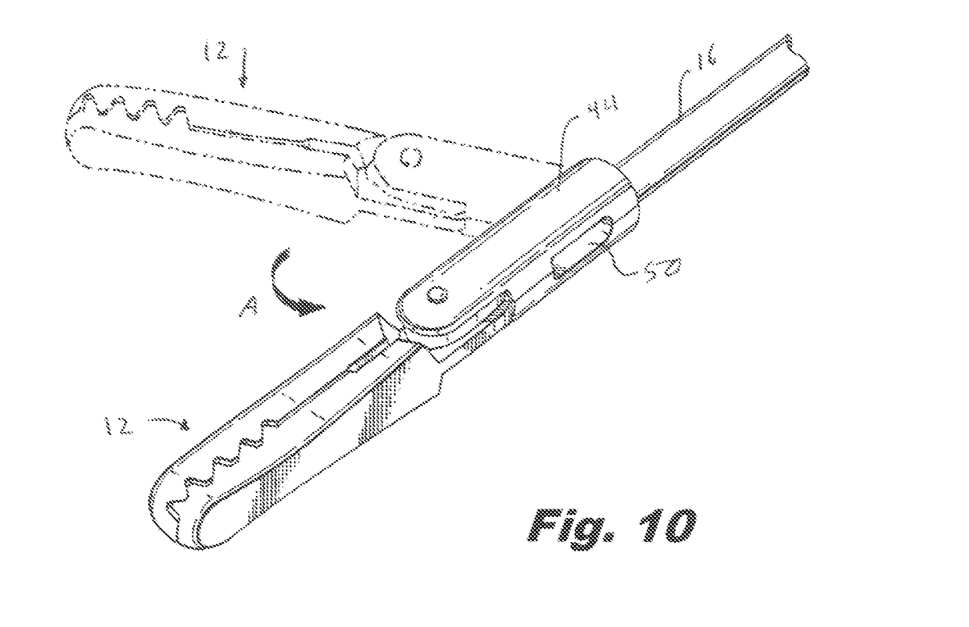
FIG. 10 is a perspective view of the end effector being rotated into engagement with a distal end of the surgical instrument.
Figure 11:
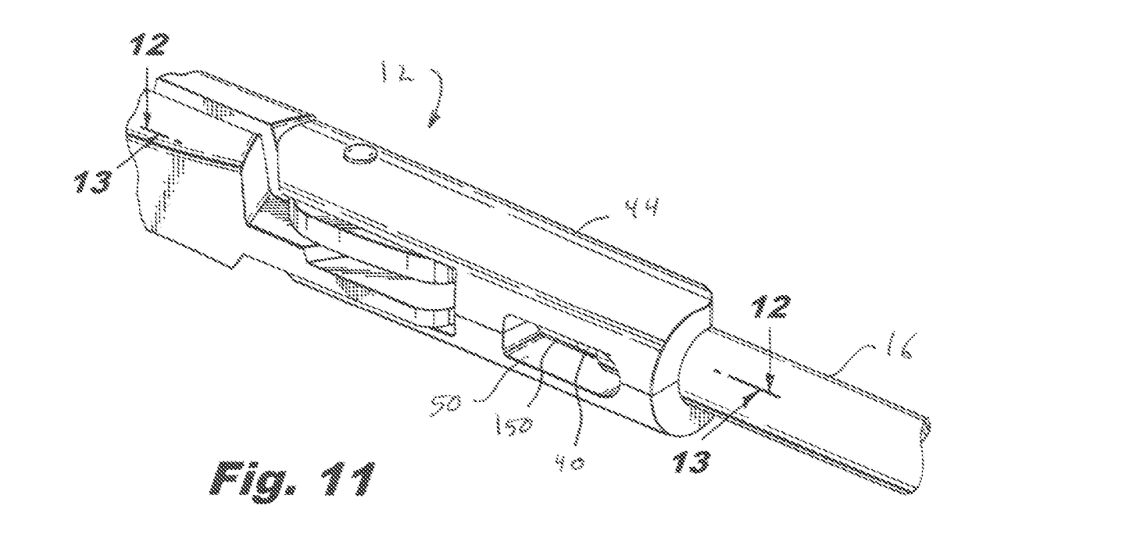
FIG. 11 is a perspective view of the end effector connected to the surgical instrument.

As best shown in FIG. 10, end effector 12 is rotated in the direction of arrow "A" from its initial position at approximately 90° relative to elongate tubular member 16 to a final position substantially in line with elongate tubular member 16 where disk 150 has fully passed through slot 50 in base 44 of end effector 12 (FIGS. 10 and 11).

Figure 12:
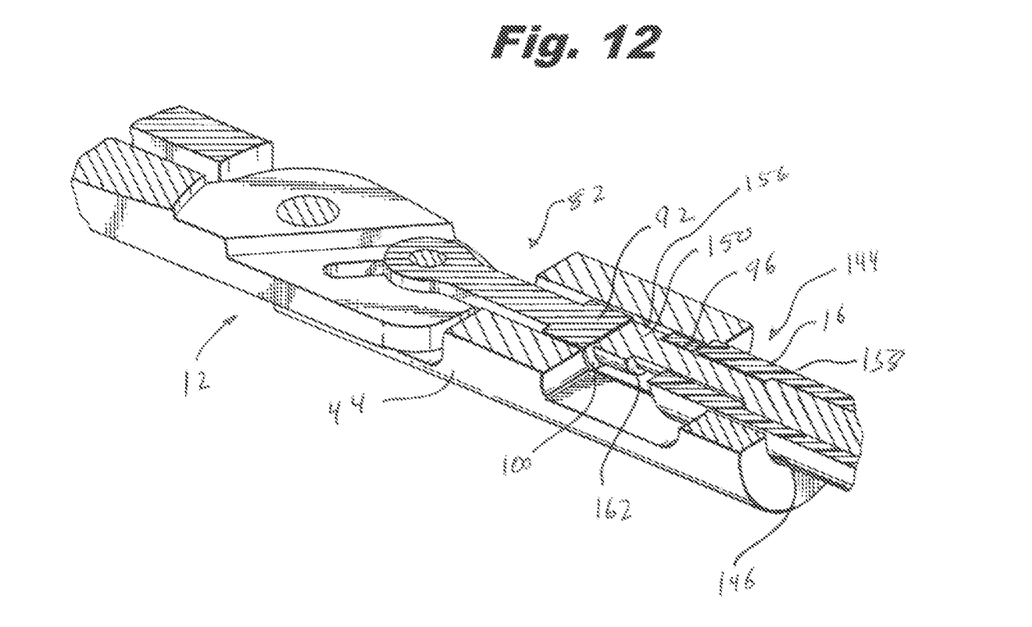
FIG. 12 is a perspective, cross-sectional view taken along line 12-12 of FIG. 11.
Figure 13:
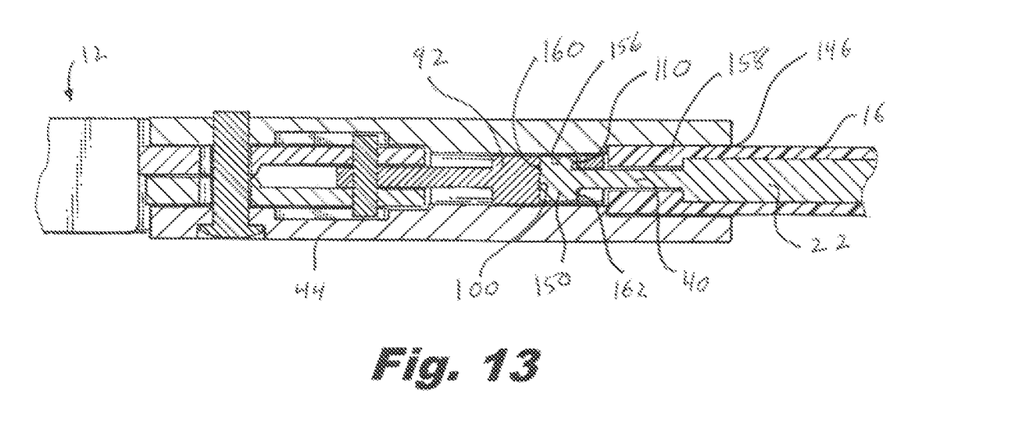
FIG. 13 is a cross-sectional view taken along line 13-13 of FIG. 11.

Turning now to FIGS. 12 and 13, as end effector 12 is rotated into position, a distal end portion 158 of elongate tubular member 16 passes through side opening 144 in base 44 and extends into base 44 through proximal opening 146. In the fully engaged condition, a distal driving surface 160 of disk 150 abuts and engages driven surface 100 on driving disk 92 of coupler 82. A proximal drawing surface 162 of disk 150 abuts and engages a drawn surface 110 on collar 96 of coupler 82. Thus, disk 150 of center rod 22 engages coupler 82 in snap fit fashion. In this position, disk 150 is locked into engagement within pocket 156 of coupler 82. Proximal tension on center rod 22, due to compression spring 32 (FIG. 1), further assists in maintaining disk 150 within pocket 156.

As shown in FIGS. 12 and 13, coupler 82 is in an initial, proximal position. Drive pin 88 is in a proximal position within drive slots 62 and 74 and jaws 46 and 48 are in the closed position substantially adjacent each other.

Figure 14:
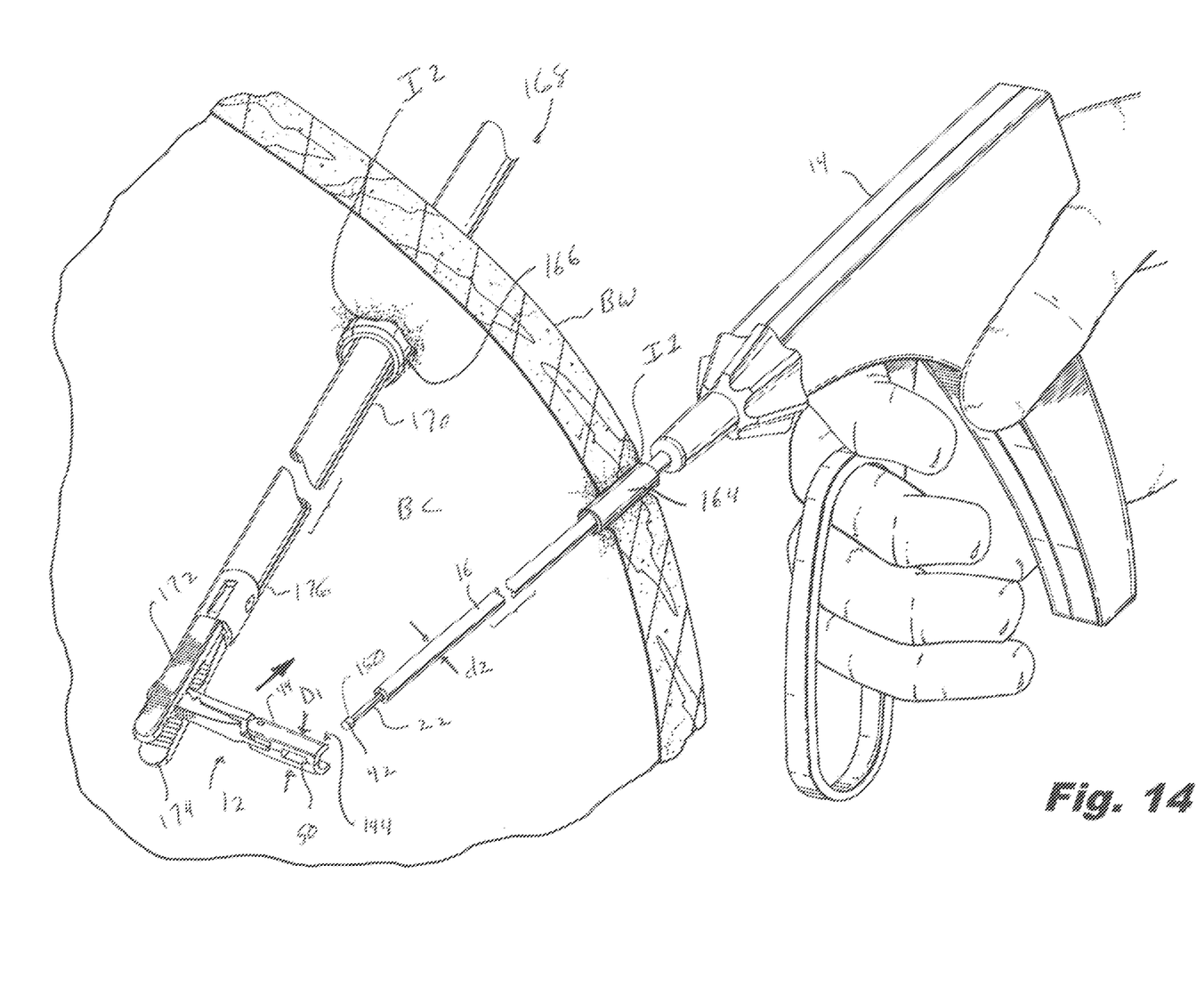
FIG. 14 is a perspective view of a laparoscopic surgical instrument and the disclosed end effector being separately inserted into a body cavity.

Referring now to FIGS. 14-17, the operation of surgical instrument 10 and method of remotely attaching end effector 12 to elongate tubular member 16 and center rod 22 will now be described. Referring initially to FIG. 14, a first incision I1 is made through a body wall BW of a patient to access an operative site within a body cavity BC and a first cannula 164 is inserted through first incision I1. First cannula 164 has a through bore or lumen 166 for receipt of elongate tubular member 16. Alternatively, elongate tubular member 16 may be inserted directly through first incision I1 to minimize the size of first incision I1 and take advantage of the small diameter d2 of elongate tubular member 16 (FIG. 1). Elongate tubular member 16 is inserted through first cannula 164 until distal tip 42 of center rod 22 is positioned within body cavity BC. In a preferred method, elongate tubular member 16 has an outer diameter of 2.7 mm and is inserted through a 2.7 mm skin incision.

In order to attach end effector 12 having a greater diameter D1 than elongate tubular member's diameter d2, a second, larger incision I2 is made through body wall BW and a second larger cannula 166 is inserted through second incision I2. Second larger cannula 166 is approximately 10 mm. A grasping instrument 168 is provided to insert end effector 12 through second cannula 166 and manipulate end effector 12 within body cavity BC. In this embodiment, D1 of end effector 12 is 5 mm. Grasping instrument 168 includes a shaft 170 having first and second jaws 172 and 174 pivotally mounted on a distal end 176 of shaft 170.

End effector 12 is grasped between first and second jaws 172 and 174 and is inserted into body cavity BC through second cannula 166. Thereafter, end effector 12 is manipulated to be in a position at a substantially right angle to elongate tubular member 16. While the disclosed angle of approach is substantially a right angle, it should be appreciated that end effector 12 may approach elongate tubular member at other angles without requiring that end effector 12 be directly in line with elongate tubular member 16 to initially connect them together.

Figure 15:
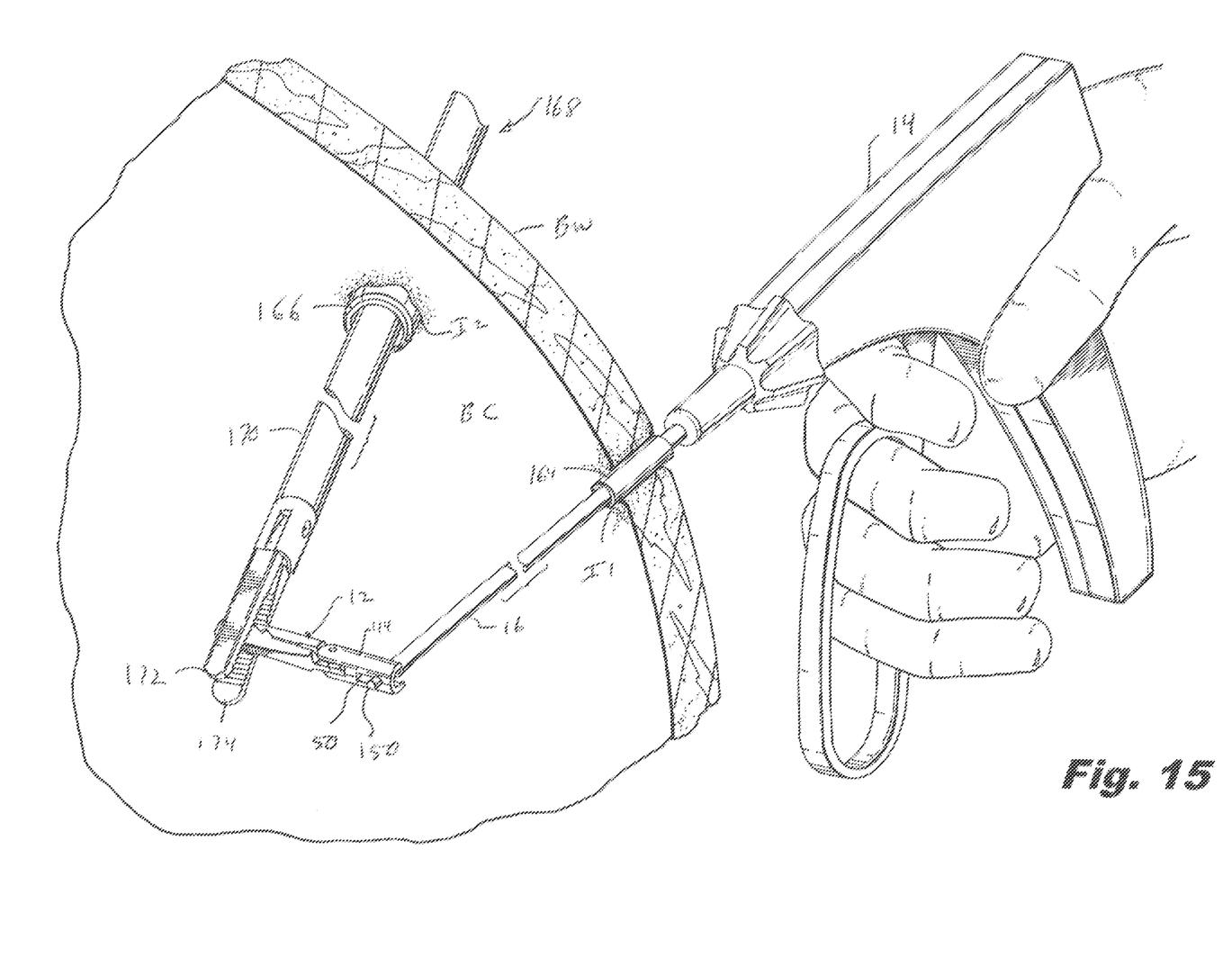
FIG. 15 is a perspective view of the end effector being initially engaged with the distal end of the surgical instrument.

With reference to FIGS. 14 and 15, grasping instrument 168 is manipulated to move end effector 12 toward and over center rod 22 and against elongate tubular member 16 such that disk 150 on center rod 22 passes through side opening 144 in base 44 of end effector 12 and passes through slot 50 in base 44. As noted above, in this position, distal face 152 of elongate tubular member 16 abuts outer surface 154 of base 44 (FIG. 9).

Figure 16:
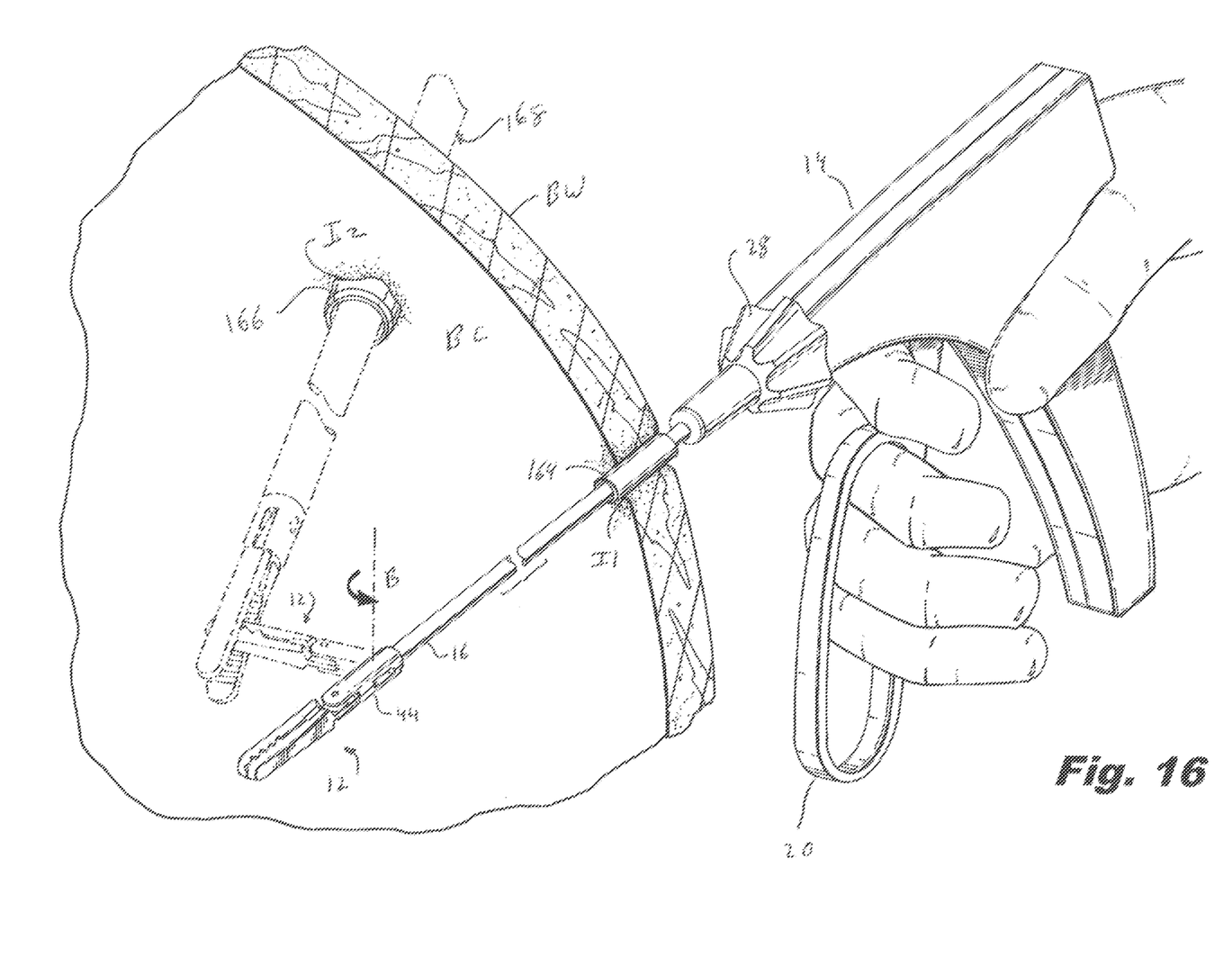
FIG. 16 is a perspective view of the end effector being rotated into full engagement with the surgical instrument.

Turning now to FIG. 16, the attachment of end effector 12 to center rod 22 and elongate tubular member 16 is completed by manipulating and rotating end effector 12 in the direction of arrow B to bring end effector 12 into longitudinal alignment with elongate tubular member 16 complete the connection. More importantly, rotating end effector 12 forces disk 150 into snap fit engagement within pocket 156 of coupler 82 and causes distal end 158 of elongate tubular member to pass through proximal opening 146 in base 44 as described hereinabove with regard to FIGS. 8-13. Proximal tension is applied to center rod 22 by compression spring 32 to further lock disk 150 within pocket 156.

Figure 17:
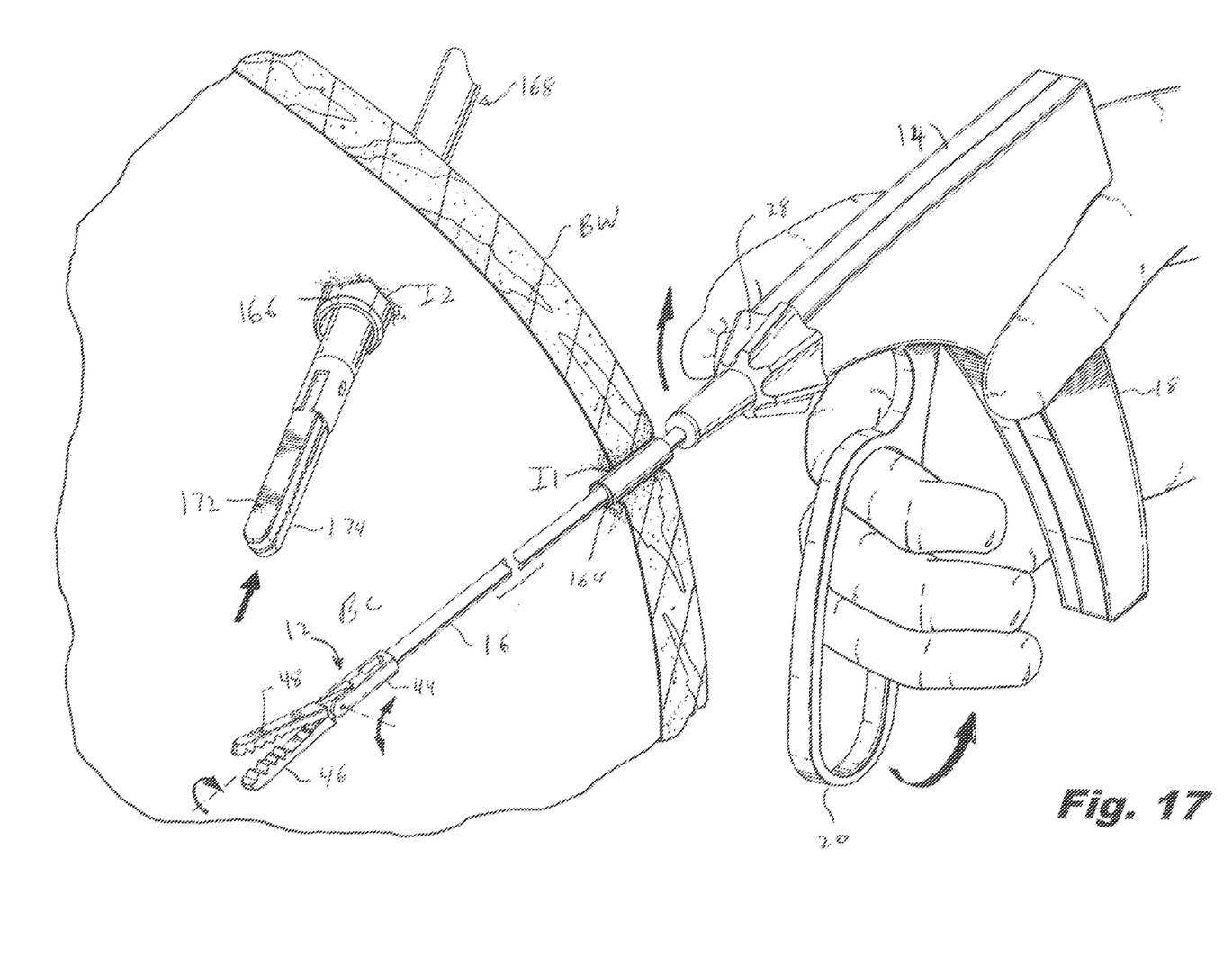
FIG. 17 is a perspective view of the surgical instrument with the attached end effector in operation.

Referring to FIG. 17, once end effector 12 has been attached to center rod 22 and elongate tubular member 16, end effector 12 is released from first and second jaws 172 and 174 of grasping instrument 168, and grasping instrument 168 can either be removed through second cannula 166 or may remain in position to further assist with an operation in body cavity BC.

Surgical instrument 10 is operated by rotating first and second jaws 46 and 48 of end effector 12 through manipulation of rotation knob 28. Once properly oriented, trigger 20 is actuated by compressing it toward handle housing 18. As noted above, compressing trigger 20 drives center rod 22 distally within elongate tubular member 16 against the bias of compression spring 32 (FIG. 1). As center rod 22 moves distally, driving surface 160 on disk 150 of center rod 22 forces driven surface 100 on driving disk 92 of coupler 82 distally to move drive link 84 and drive pin 88 distally (FIGS. 12 and 13). Drive pin 88 moves distally through drive slots 62 and 74 of first and second jaws 46 and 48 (FIG. 2) to cam first and second jaws 46 and 48 between the closed position to an open position substantially spaced apart to grasp tissue.

In order to close first and second jaws 46 and 48, trigger 20 is moved away from handle housing 18 to draw center rod 22 proximally within elongate tubular member 16. Additionally, simply removing pressure from trigger 20 allows compression spring 32 to bias center rod proximally. Proximal movement of center rod 22 causes drawing surface 162 on disk 150 of center rod 22 to pull proximally on drawn surface 110 of collar 96 of coupler 82 (FIGS. 12 and 13) thereby pulling drive pin 88 proximally through drive slots 62 and 74 to move first and second jaws 46 and 48 from the open to the closed positions.

In this manner, surgical instrument 10 provide a system and method of remotely attaching an end effector 12 to a handle assembly 14 without having to initially longitudinally align end effector 12 with elongate tubular member 16. It additionally provides a method of attaching an end effector 12 having a relatively large diameter to a shaft or elongate tubular member 16 having a smaller diameter.

It will be understood that various modifications may be made to the embodiments disclosed herein. For example, the distal tip of the center rod can take other shapes such as, for example, block, ball, triangular wedge, etc. Further, the end effector can include a single jaw grasper, a single or pair of pivotal or extendable cutting blades, movable cautery blades or members etc. for operation through the disclosed coupler. Additionally, the center rod may be spring biased distally by a compression spring to maintain engagement with the coupler. Therefore, the above description should not be construed as limiting, but merely as exemplifications of particular embodiments. Those skilled in the art will envision other modifications within the scope and spirit of the claims appended hereto.

The invention claimed is:

1. An end effector for remote attachment to a distal end of a surgical instrument comprising:
   a base;
   a drive pin movably mounted on the base, the drive pin longitudinally translatable relative to the base; and
   a coupler movably positioned within the base and connected to the drive pin, the coupler having a side opening for receiving a center rod of the surgical instrument.

2. The end effector as recited in claim 1, wherein the base includes a first slot formed through a first side of the base.

3. The end effector as recited in claim 2, wherein the base includes a second slot formed through a second side of the base.

4. The end effector as recite in claim 3, wherein the base includes a proximal opening.

5. The end effector as recited in claim 1, wherein the coupler includes a link connected to the drive pin.

6. The end effector as recited in claim 1, wherein the coupler includes a distal portion and a collar proximal to the distal portion, the distal portion and the collar defining the pocket therebetween.

7. The end effector as recited in claim 6, wherein the distal member is a disk and the coupler includes a web portion connecting the disk to the collar.

8. The end effector as recited in claim 6, wherein the collar is C-shaped and defines the side opening for passage of the center rod of the surgical instrument.

9. A surgical instrument for remote assembly within the body of a patient comprising:
   a handle housing;
   an elongate tubular member extending distally from the handle housing to a distal end thereof;
   a center rod movably mounted within the handle housing and elongated tubular member and having a distal tip and a groove proximal the distal tip, a distal portion of the center rod extending beyond a distal end of the elongate tubular member; and
   an end effector having a base, a drive pin movably attached to the base, and a coupler connected to the drive pin and defining a pocket for receipt of the distal tip of the center rod, the coupler having a side opening for receiving the center rod.

10. The surgical instrument as recited in claim 9, wherein the pocket is defined between a distal disk of the base and a proximal C-shaped collar of the base.

* * * * *

UNITED STATES PATENT AND TRADEMARK OFFICE
CERTIFICATE OF CORRECTION

| | | |
|---|---|---|
| PATENT NO. | : 9,023,015 B2 | Page 1 of 1 |
| APPLICATION NO. | : 13/756777 | |
| DATED | : May 5, 2015 | |
| INVENTOR(S) | : Christopher Penna | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 132 days.

Signed and Sealed this
Twentieth Day of October, 2015

Michelle K. Lee
*Director of the United States Patent and Trademark Office*